United States Patent [19]

Nagel et al.

[11] 4,338,303
[45] Jul. 6, 1982

[54] TREATMENT OF PARASITIC DISEASES

[75] Inventors: Ronald L. Nagel, New York; Carmen E. Raventos, New Rochelle, both of N.Y.

[73] Assignee: Albert Einstein College of Medicine of Yeshiva University, Bronx, N.Y.

[21] Appl. No.: 118,186

[22] Filed: Feb. 4, 1980

[51] Int. Cl.³ .................. A61K 33/00; A61K 31/275
[52] U.S. Cl. .................................. 424/129; 424/304
[58] Field of Search ............................. 424/129, 304

[56] References Cited

U.S. PATENT DOCUMENTS 3,833,724  9/1974  Cerami et al. ...................... 424/129

Primary Examiner—Sam Rosen
Attorney, Agent, or Firm—Stephen E. Feldman; Marvin Feldman; Steve T. Zelson

[57] ABSTRACT

A method is disclosed herein for the treatment of parasitic diseases in animals such as birds and mammals, more specifically, in vivo and in vitro treatments of malaria, chagas disease and sleeping sickness with a compound comprising a unit of the formula:

$$R_1-[-O-C\equiv N]$$

wherein the N may be single, double or triple bonded with respect to C, wherein $R_1$ is one selected from the group consisting of alkali metals, ammonium and low molecular weight organo groups selected from the group consisting of alkyl, aryl, aroalkyl and allyl groups, whereby said parasitic infection is either reduced in severity or entirely eliminated. The compounds may comprise isocyanates, cyanate salts and carbamylphosphates.

9 Claims, 5 Drawing Figures

TREATMENT OF PARASITIC DISEASES

FIELD OF THE INVENTION

This invention relates to a method for treating and curing various parasitic diseases of birds and mammals.

DESCRIPTION OF THE PRIOR ART

Malaria, sleeping sickness and chagas disease are infectious diseases caused by any of various protozoa such as *Plasmodium vivax, Plasmodium falciparum, Plasmodium malariae* and *Plasmodium ovale* and trypanosoma protoza. Malarial infecting agents are parasitic in red blood corpuscles and are transmitted to birds and mammals by the bite of an infected Amopheles mosquito. The malaria parasite is one of the most important of human pathogens. The trypanosoma protozoa are also parasitic in the blood stream of mammals and may be transmitted by the bite of a tsetse fly.

The prior art treatment of *P. falciparum* malaria in humans with chloroquine compound has been generally successful, but in recent years serious problems have arisen, see Center for Disease Control: Chemoprophylaxis of Malaria Morbidity Mortality Weekly Rep., 27 (Suppl.) 81-90 (1978). One problem is that the number of chloroquine resistant species is increasing in areas with already high incidence of the varients namely, Southeast Asia, Indonesia, Panama, and parts of the Indian subcontinent. See World Health Organization, W.H.O. Chronicles, 32, 9-17, (1978). In addition, chloroquine-resistant species have recently been reported for the first time in East Africa previously devoid of these mutants, See Fogh, S. et al, Trans. Royal Soc. Trop. Med. and Hygiene, 73, 228-229 (1979). The most commonly used alternative treatments, namely, quinine, primethamine and sulfadiazine, have shortcomings including adverse side-effects (some of them serious), as well as cost and availability. In addition, the use of primaquine for the eradication of the exoerythocytic forms in Ovale and Vivax malaria, is not recommended in glucose-6-phosphate dehydrogenase deficiency, a condition that has a high incidence among Blacks and some Caucasian ethnic groups, see Clyde, D. F., Bull. W.H.O, 50, 243-249 (1974).

The prior art was desirous of finding a possible new composition for treatment of these parasitic diseases. Previously certain cyanates were used for the treatment of sickle cell anemia, such as in U.S. Pat. No. 3,833,724, granted Sept. 3, 1974.

It is therefore a principal object of the present invention to provide a method as aforesaid which may be used in conjunction with parasitic disease causing agents.

It is another object of this invention to provide a method for a simplified and inexpensive treatment of parasitic diseases with a compound, a mixture or complex containing isocyanates, carbamylphosphates or cyanate salts.

It is a further object of this invention to provide a method for the in vivo or in vitro treatment of animals such as mammals and birds, for parasitic diseases.

The aforesaid as well as other objects and advantages will become apparent from a reading of the following description and adjoined claims.

DESCRIPTION OF THE PREFERRED EMBODIMENT

Figure 2A:
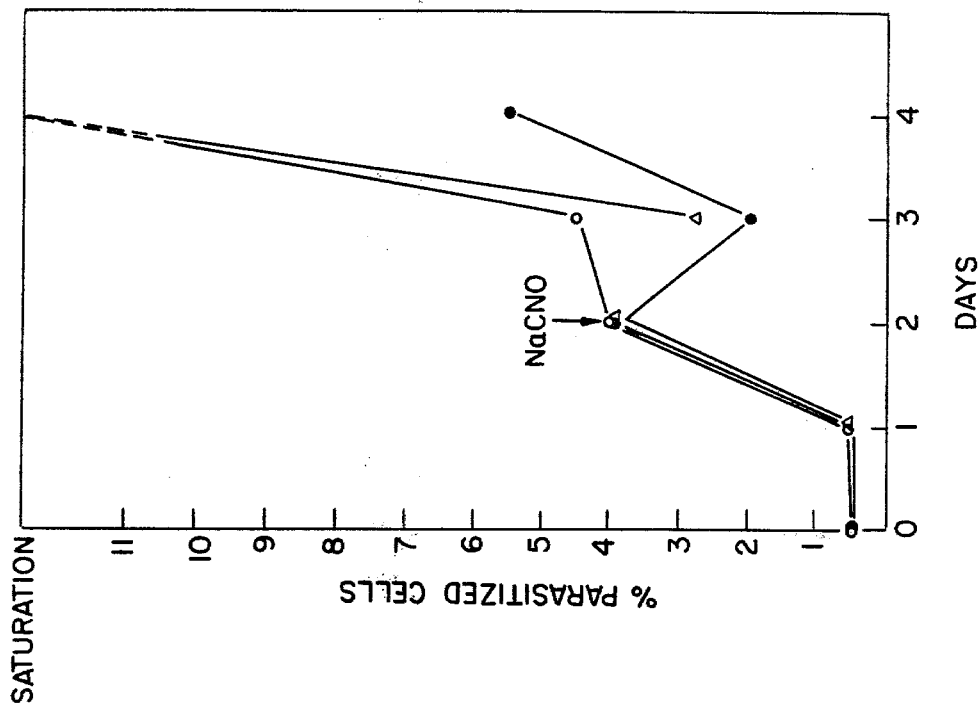
FIG. 2a shows the effect of a pulse addition of NaCNO on almost exclusively late trophozoites in a synchronized *P. falciparum* culture.

Broadly speaking, this present invention is a method for treatment of parasitic diseases in animals with a compound comprising a unit having the formula—O—C.N, wherein the N may be single, double or triple bonded to the C, whereby the parasitic disease undergoes remission or complete elimination. This unit will be called NCO in the rest of this application.

Broadly speaking in another aspect this present invention comprises the treatment of parasitic diseases with isocyanates, cyanate salts and carbamylphosphates. More specifically, this invention may be said to be a method for the treatment of malaria, chagas disease and sleeping sickness in animals such as mammals and birds caused by any of various protozoa infecting agents such as *Plasmodium vivax, Plasmodium falciparum, Plasmodium malariae* and *Plasmodium ovale* and trypanosoma protozoa by either in vivo or in vitro exposure of said protozoa infecting agents to a substance, compound, mixture or complex which, at least in part, comprises a compound with the formula —[—O—C.N] wherein the N may be single, double or triple bonded with respect to C. More specifically, compounds of this formula may be selected from the group consisting of:

$$R_1-O-C\equiv N; \quad (1)$$

$$R_1-O-C=N-R_2; \quad (2)$$

and

$$R_3-O-C-N\begin{smallmatrix}R_2\\\\R_2\end{smallmatrix} \quad (3)$$

wherein $R_1$ is one selected from the group consisting of alkali metals, ammonium and low molecular weight organo groups, $R_2$ is one selected from the group consisting of H and low molecular weight organo groups and $R_3$ is one selected from a low molecular weight organo group, a phosphorous group or organo phosphorous group. Examples of compound (1) may be, but are not necessarily limited to, cyanate salts such as sodium cyanate, potassium cyanate and ammonium cyanate. Examples of compound (2) may be, but are not necessarily limited to isocyanates, such as methylisocyanate, propylisocyanate and ethylisocyanate. An example of compound (3) may be, but is not necessarily limited to carbamylphosphate. The low molecular weight organo groups herein may comprise an alkyl, aryl, aroalkyl, allyl and substituted groups thereof, wherein the preferred is an alkyl of $C_1$–$C_8$. The isocyanates, carbamylphosphate and cyanate salts may also be utilizable with excorporeal modes of delivery wherein the blood removed from the effected animal is treated with the above compounds, is then dialized, and finally is refused into the animal.

It has surprisingly been found that treating a parasitic infected animal system with isocyanates, carbamylphosphate or cyanate salts, such as sodium cyanate, the survivability of the disease causing infection agent is directly effected. With the dosages and treatment periods dependent upon the compound chosen and the individual characteristics of the animal being treated, the severity of the disease can be greatly decreased and even a complete 100% remission is both possible and probable. It is also probable that the method disclosed herein is applicable for treatment of other parasitic diseases in birds and/or mammals.

The following example is illustrative of the invention.

EXPERIMENTAL EXAMPLE 1

The FCR-3 strain of *P. falciparum* was obtained from Dr. J. B. Jensen, Rockefeller University, N.Y.C. and was maintained in culture utilizing the candle-jar method. See Jensen, J. B. et al, J. of Parasit., 63, 883–886 (1977).

In order to obtain non-synchronized cultures (cultures wherein the red blood cells infected with the parasite are not in the same stage of the disease), a suspension of 0.5% parasitized cells first was prepared by adding fresh washed uninfected cells to a stock culture containing approximately 10% parasitized cells. Complete medium was then added in order to obtain a 8% erythrocyte suspension. Four ml of this suspension was then placed into 60×15 mm plastic tissue culture petri dishes (Falcon) in triplicate.

In order to obtain synchronized cultures (cultures wherein all the red blood cells infected with the parasite are in the same stage of the disease) the parasitized cells were allowed to grow for 5 days. The cells were, after 5 days, characterized by "saturation" features: the number of parasitized cells decreases (having reached a population density of 10-15%) and a number of degenerated forms can be observed. These characteristics will appear earlier in the culture, if for example, feeding of fresh medium is increased in frequency.

The "saturated" cultures have scyizonts (parasite developing within a red blood cell) not capable of completing schizogony. If this "saturated" culture is diluted to 1% of parasitized cells with fresh washed red cells and incubated for 18 hrs. a generation of synchronized ring form is observed.

Recrystallized NaCNO (Diamond-Shansock, Baltimore, Md.) was dissolved in medium and sterilized by filtration through 0.45 Nalgene Filters just before adding the solution to the cultures.

In one series of tests infected red cells were exposed to a short pulse of NaCNO. Parasitized cells were diluted with complete medium containing 50 mM and 25 mM/ml of NaCNO and incubated for 30 minutes at 37 degrees C. The cells were then spun at 1500 rpm for 10 minutes at 25 degrees C. in an International Centrifuge and the media was discarded. The cells were subsequently washed 3 times in drug and serum-free media, resuspended in complete media and placed back into culture. Similar tests were conducted in synchronized culture.

In another series of tests, concentrations of NaCNO ranging from 10 to 0.1 mM/ml were added to the culture for a full 48 hour period (one cycle). During this period the culture was changed at usual intervals with medium containing the same amount of cyanate. At the end of the 48 hour period, the cells were diluted with drug-free medium.

To distinguish between the effect of cyanate on hemoglobin and the red cell membrane and its effects on the intraerythrocytic parasite, red cells were pre-treated for 30 minutes with 50 mM NaCNO, washed and used to dilute the infected culture. The parasite growth in these host cells was then recorded.

Figure 1:
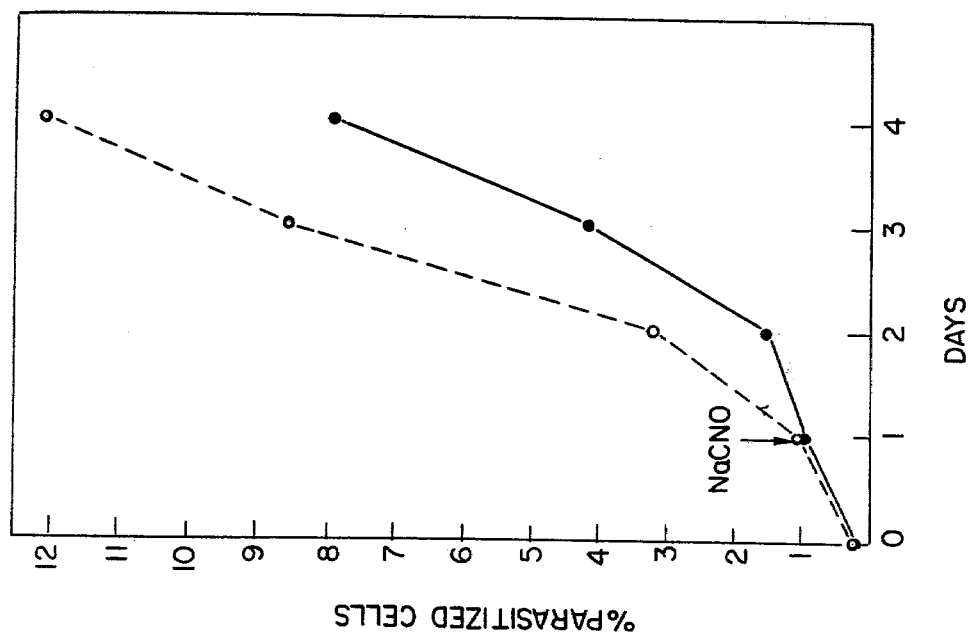
FIG. 1 shows the effect of a pulse of NaCNO on a nonsynchronized *P. falciparum* culture.

FIG. 1 illustrates the pulse addition (30 minutes incubation) of 50 mM CaCNO to a non-synchronized culture of *P. falciparum* on the first day of the culture. A significant decrease in the rate of growth of the culture is observed immediately after the treatment with cyanate.

Figure 2B:
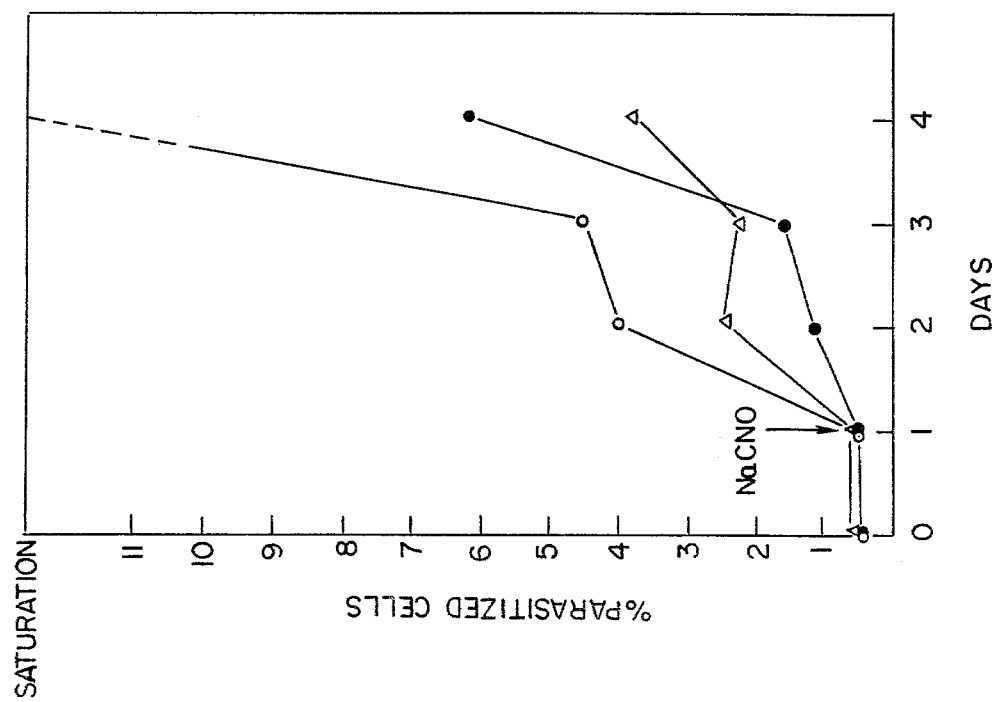
FIG. 2b shows the effect of a pulse addition of NACNO on predominantly early trophozoites in a synchronized *P. falciparum* culture.

FIG. 2a and b illustrates the effect of the pulse addition of 50 mM and 25 mM concentration of NaCNO, when the synchronized culture is predominantly late trophozoites (later development form of intraesythrocytic parasite) or schizonts (FIG. 2a) or when the culture is predominantly ring forms (early trophoziotes) (FIG. 2b). In both instances, a clear reduction in the rate of growth of the parasite is observed. The effect is greater with 50 mM than with 25 mM, and the culture seems to resume its growth potential in the post-pulse period, particularly with the lower doses.

Figure 3:
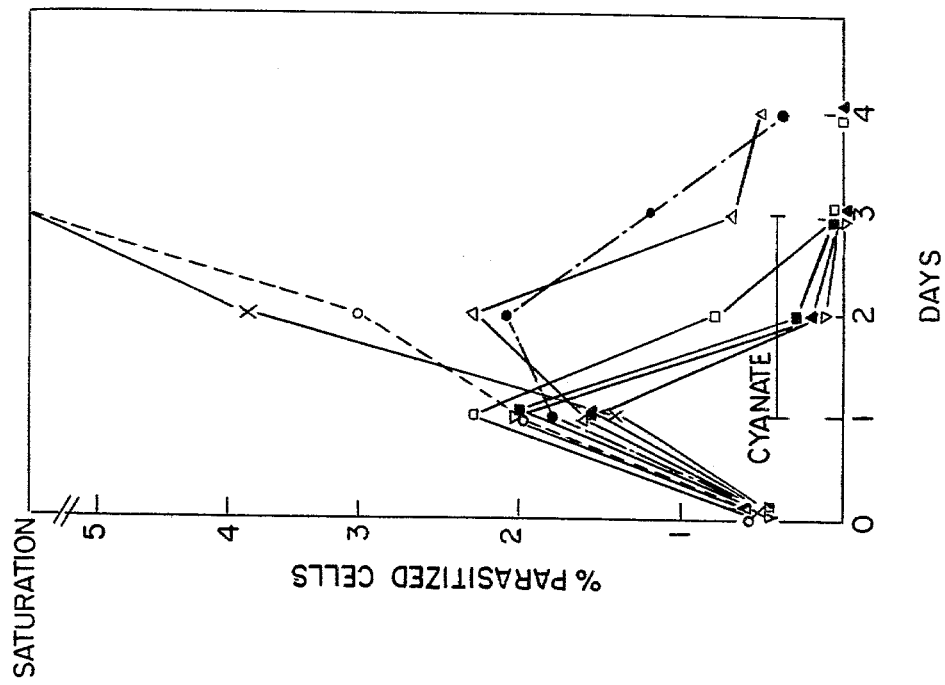
FIG. 3 shows the effect on NaCNO during 48 hours, on *P. falciparum* in non-synchronized cultures.

FIG. 3 illustrates the effect of several concentrations (10 mM to 0.1 mM) of NaCNO on the growth of *P. falciparum*. In these tests cyanate was in contact with the red cells in the culture for 48 hours. Concentrations above 1.0 mM destroyed the cultures and no parasitized forms were observed in day 3 and 4. Concentrations of 1.0 and 0.5 mM had a significant inhibitory effect but did not obliterate the culture. Cyanate at a concentration of 0.1 mM had no effect.

Figure 4:
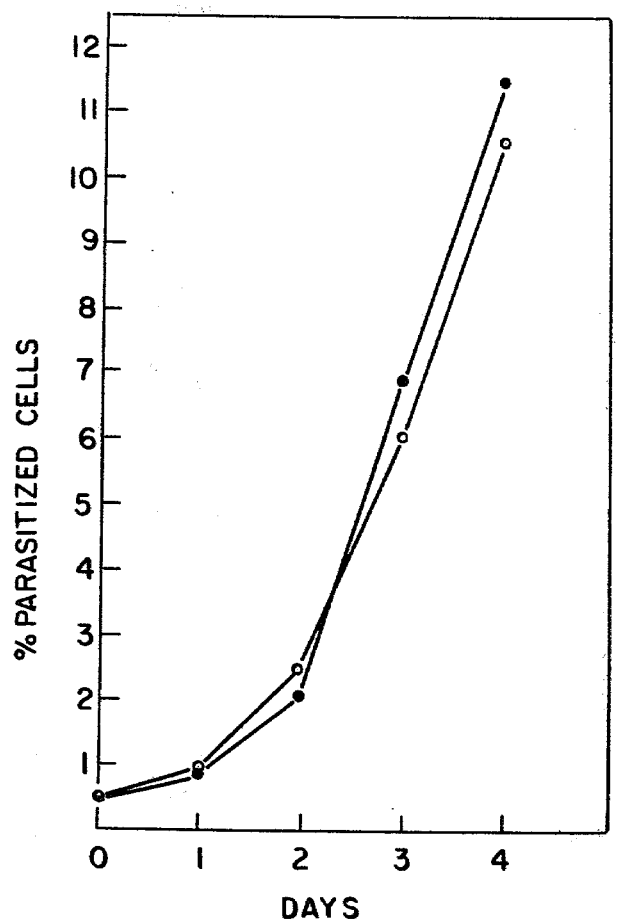
FIG. 4 shows the effect of pre-treatment of red cells with 50 mM NaCNO on the growth of *P. falciparum*.

Red cells treated with 50 mM cyanate prior to infection sustained the growth of the parasite just as well as untreated cells (FIG. 4).

FIG. 1. Effect of a pulse of NaCNO on a non-synchronized *P. falciparum* culture. —o—o — control; —●—●— 30 min. pulse of 50 mM NaCNO; ordinate: % of parasitized cells; abcissa: age of the culture.

FIG. 2: Effect of a pulse of NaCNO on a synchronized *P. falciparum* culture. Days 1 and 3 of the culture are almost exclusively late trophozoites and days 2 and 4 are almost exclusively ring forms (early trophozoities). a. Effect of a pulse addition of NaCNO on almost exclusively late trophozoites; —o—o— control; —Δ—Δ— 25 mM NaCNO; —●—●— 50 mM NaCNO. b. Effect of a pulse addition of NaCNO on predominantly early trophozoites (ring forms) —o—o— control; —Δ—Δ— 25 mM NaCNO; —●—●— 50 mM NaCNO.

FIG. 3: Effect of additions of NaCNO during 48 hrs. on *P. falciparum* non-synchronized cultures. —x—x— control; —o—o—O. mM; —●—●— 0.5 mM; —Δ—Δ— 1.0 mM —▲—▲— 2.0 mM; —□—□— 5.0 mM; —■—■— 8 mM; —∇—∇— 10.0 mM. Saturation: see text.

FIG. 4: Effect of the pre-treatment of red cells with 50 mM NaCNO on the growth of *P. falciparum*. —o—o— control; —●—●— 50 mM NaCNO.

The data disclosed herein demonstrates that sodium cyanate is capable of inhibiting the intraerythrocytic growth of *P. falciparum*. At various concentrations the parasite fails to develop and appears to have been killed. In addition, both early (ring) and late trophozoite are inhibited by cyanate. The lack of effect of the pre-treatment of red cells by cyanate on the growth pattern of the parasite suggests that the mechanism of inhibition is not mediated by carbamylation of hemoglobin or the red cell membrane. A direct carbamylation of critical proteins in the parasite, seems to be the most likely explanation for this effect. Cyanate is known to carbamylate readily (at neutral pH), with amino terminal groups and some amino groups of lysine in proteins (see Stark, G. R. et al, J. Biol. Chem., 235, 3177-3181 (1960)).

The inhibitory effect of cyanate is obtained in vitro at concentration levels of 0.5 mM. Per os administration of cyanate can attain blood levels of about 0.4 mM with doses of 900 mg (22 mg/Kg) (see Nigen, A. N. et al, J. Pharmac. and Exp. Therapeut, 195, 333-330, (1975)). Intravenous administration of the drug at doses of 30 mg/Kg can reach blood concentration of about 0.8 mM (see Nigen, A. M. et al J. Lab. Clin. Med., 83, 139-146 (1974). Finally, extracorporeal delivery of cyanate has been recently developed (see Dietrich, D. et al, In Erythrocyte Structure and Function (Brewer, G. J. ed.) Allen R. Less, Inc., N.Y. (1955)) and could be still another therapeutic modality that could be useful for selected indications in the treatment of malaria.

No short-term side effects have been observed in individuals receiving cyanate in doses less than 30 mg/KG. Long term complications (polyneuritis and cataracts) were observed during trails of this drug as an antisickling agent, only after several months of administration and mostly with the higher doses (35 mg/Kg) (see Harkness, D. R. et al, Prog. Hematol., 9, 157-184 (1955)). In the case of malaria, cyanate would probably be used for short treatment periods in which no side effects have been observed.

In conclusion, cyanate appears to inhibit the growth of *P. falciparum* in human red cells and indicates that it should be an effective agent in the treatment of malaria and other related parasitic diseases.

What is claimed is:

1. A method for treating a protozal parasitic disease in an animal comprising exposing the protozoal parasitic infecting agents of said diseased animals to an effective amount of the compound which comprises $R_1$—[O—C≡N] wherein $R_1$ is one selected from the group consisting of alkali metals, ammonium and low molecular weight organo groups selected from the group consisting of alkyl, aryl, aroalky, and allyl groups.

2. The method of claim 1, wherein the animal is a mammal.

3. The method of claim 1, wherein the animal is a bird.

4. The method of claim 1, wherein the exposure of the protozoa parasitic infecting agent to said compound occurs in vivo.

5. The method of claim 1, wherein the exposure of the protozoa parasitic infecting agent to said compound occurs in vitro.

6. The method of claim 1, wherein the protozoa parasitic disease is one selected from the group consisting of malaria, sleeping sickness and chagas disease.

7. The method of claim 1, wherein the protozoa parasitic infecting agent is one selected from the group consisting of *Plasmodium vivax*, *Plasmodium falciparum*, *Plasmodium malariae*, *Plasmodium ovale*, and trypanosoma protozoa.

8. The method of claim 1, wherein the low molecular weight organo group is an alkyl of from $C_1$ to $C_8$.

9. The method of claim 1, wherein the compound is one selected from the group consisting of sodium cyanate, potassium cyanate and ammonium cyanate.

* * * * *